(12) United States Patent
Phillips

(10) Patent No.: US 6,641,741 B2
(45) Date of Patent: Nov. 4, 2003

(54) REMOVAL AND RECOVERY OF CHLORIDE FROM PHOSPHONOMETHYLIMINODIACETIC ACID PROCESS BRINE

(75) Inventor: Scott G Phillips, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 102 days.

(21) Appl. No.: 09/834,850

(22) Filed: Apr. 13, 2001

(65) Prior Publication Data

US 2002/0148786 A1 Oct. 17, 2002

(51) Int. Cl.[7] .................................................. C02F 1/04
(52) U.S. Cl. ........................ 210/710; 159/47.3; 210/712; 210/721; 210/724; 210/737; 210/772; 210/774; 423/499.5; 562/16; 562/17
(58) Field of Search ................................. 210/724, 712, 210/718, 721, 710, 737, 758, 763, 766, 772, 774; 159/47.3; 423/499.4, 499.5; 562/11, 16, 17

(56) References Cited

U.S. PATENT DOCUMENTS 3,904,520 A * 9/1975 Dancy ........................... 209/5
4,687,842 A * 8/1987 Henzi ........................ 534/573
4,775,498 A * 10/1988 Gentilcore .................... 562/17
6,118,022 A * 9/2000 Cullen ......................... 562/16
6,265,605 B1 * 7/2001 Johnson et al. ............... 562/14

FOREIGN PATENT DOCUMENTS

| EP | 0155926 A | 9/1985 |
| EP | 0323821 A | 7/1989 |
| EP | WO9415939 A | 7/1994 |
| EP | WO9640592 A | 12/1996 |
| EP | WO0059915 A | 10/2000 |
| GB | 2154588 A | 9/1985 |

OTHER PUBLICATIONS

Mark H.F. et al, "Kirk–Othmer Encyclopedia of Chemical Technology", Edition 3, vol. 24, p. 245 1978.

* cited by examiner

Primary Examiner—Peter A. Hruskoci
(74) Attorney, Agent, or Firm—Craig E. Mixan

(57) ABSTRACT

Chloride is selectively isolated as NaCl from N-phosphonomethyliminodiacetic acid process wastes by evaporative crystallization of the caustic neutralized brine.

7 Claims, No Drawings

REMOVAL AND RECOVERY OF CHLORIDE FROM PHOSPHONOMETHYLIMINODIACETIC ACID PROCESS BRINE

BACKGROUND OF THE INVENTION

The present invention relates to a method for effectively removing and recovering chloride from N-phosphonomethyliminodiacetic acid process wastes. More particularly, the present invention involves neutralization of the waste stream with sodium hydroxide (NaOH) and evaporative crystallization of sodium chloride (NaCl).

In the commercial manufacture of the herbicide glyphosate, iminodiacetic acid (IDA) is converted to N-phosphonomethyliminodiacetic acid (PMIDA) by reaction with hydrochloric acid (HCl), phosphorous acid ($H_3PO_3$) and formaldehyde ($CH_2O$) or by reaction with phosphorus trichloride ($PCl_3$), NaOH and $CH_2O$. The process waste from this step is routinely disposed of by deep well injection. Because of the high chloride content and high volume of this waste stream, other more environmentally friendly waste treatment alternatives such as wet air oxidation or thermal incineration are economically prohibitive. It would be desirable to have a method to reduce the content of corrosive chloride and the overall hydraulic waste volumes of the PMIDA waste stream so that other methods of disposal become economically viable.

SUMMARY OF THE INVENTION

It has now been found that NaCl can be effectively removed and recovered from phosphonomethyliminodiacetic acid (PMIDA) process wastes by neutralization of the waste stream with NaOH and by evaporative crystallization. The present invention concerns a process for the removal and recovery of NaCl from a PMIDA process waste stream which comprises neutralizing the waste stream with NaOH to a pH of about 7, evaporating off water at or below atmospheric pressure at a temperature of about 40 to about 130° C. until NaCl precipitates, filtering the precipitate at a temperature of about 35 to about 110° C., and washing the precipitate with brine. Because the concentration of sodium salts of other species in the neutralized waste stream apparently lowers the solubility of NaCl in the matrix, NaCl can be removed and recovered from the PMIDA process waste stream to a surprisingly high degree of isolation and purity.

DETAILED DESCRIPTION OF THE INVENTION

The aqueous waste stream from the manufacture of PMIDA typically can contain phosphorous acid (0.3 to 2 percent by weight), phosphoric acid (0.3 to 3 percent by weight), HCl (9 to 15 percent by weight), iminodiacetic acid (IDA; 0.1 to 0.3 percent by weight), PMIDA (0.8 to 4 percent by weight), N-methyliminodiacetic acid (MIDA; 0.5 to 8 percent by weight) as well as small quantities of methanol, formaldehyde and formic acid.

In the first step of the NaCl removal and recovery process, the PMIDA aqueous waste stream is neutralized with NaOH to a pH of about 7, i.e., so that all the organic and inorganic acids, including HCl, have been converted to their respective sodium salts, NaCl and water. In order to minimize the overall hydraulic load, it is preferable to neutralize with relatively concentrated solutions of NaOH. Commercially available 50 percent NaOH is preferred for the neutralization. The heat of neutralization significantly raises the temperature of the neutralized mixture for the subsequent evaporative crystallization.

After neutralization, water is removed from the neutralized mixture until NaCl precipitates. The water is evaporated at or below atmospheric pressure at a temperature of about 40 to about 130° C., preferably at a temperature of about 60 to about 100° C. Evaporation is continued until most of the NaCl has precipitated but not so far that the slurry becomes intractable, that foaming becomes excessive or that the subsequent filtrate becomes too viscous. Generally, the amount of water equivalent to from about 35 to about 70 weight percent, preferably from about 50 to about 65 weight percent, of the neutralized mixture is stripped off. Naturally, the amount of water removed will vary with the original concentration of the neutralized waste stream and the concentration of the neutralizing base used. The exact amount of water to be removed can be easily optimized by routine experimentation with the particular waste stream being treated. Wide ranges of operating conditions are possible for the evaporation, based upon the thermal stability of the components of the waste stream and the pressure limitations of the equipment. The water vapor from the process can be condensed for potential recycle.

After evaporative crystallization, the NaCl is recovered by filtration. Because of the viscosity of the filtrate, the filtration is conducted at a temperature of about 35 to about 110° C., preferably at temperature of about 60 to about 90° C. Gravity, upstream pressure, downstream vacuum or centrifugal force can drive the filtration. The NaCl is isolated as a filter cake. The volume of the aqueous waste stream, now represented by the filtrate, is significantly reduced and, with the removal of most of the chloride content, is more amenable to other waste treatment options besides deep well disposal, such as, for example, wet air oxidation or incineration.

In the last step of the process, the NaCl filter cake is washed with brine to remove residual filtrate. While the concentration of the brine is not critical since the brine wash can be recycled to the neutralized waste stream, the use of dilute brine results in the dissolution of salt cake and the use of a saturated brine results in the rejection of additional NaCl from the brine due to the "salting out" caused by the sodium salt-containing components in the wash-displaced filtrate. Preferably, the concentration of NaCl in the wash brine should be the same as that in the filtrate. While the temperature of the wash step is not critical, the viscous residual filtrate in the filter cake can be more efficiently removed by washing at elevated temperatures, for example, from about 35 to about 60° C.

The following examples illustrate the invention.

EXAMPLES

1. In a 3-necked 250 milliliter (mL) flask equipped with a side arm water-cooled condenser and receiver, a variable-speed paddle agitator and a thermowell with a temperature controlled heating mantle and supplied with a controlled vacuum source, 100 grams (g) of a PMIDA process brine having a composition of 0.3% IDA, 6.7% MIDA, 3.8% PMIDA, 10.1% HCl, 1.8% $H_3PO_3$ and 2.2% $H_3PO_4$ was neutralized to pH=6.97 with 41.2 g of 50% NaOH. After sampling, 135.3 g of the neutralized brine was stripped at atmospheric pressure until 74.5 g of water had been removed and NaCl had precipitated. The slurry was filtered under vacuum through a coarse sintered glass filter and the filter cake was washed with 20 g of saturated brine to yield 13.5 g of white wet cake that weighed 12.0 g after drying. The dry cake assayed as 99.8% NaCl. The viscous filtrate contained 15.0% MIDA, 8.9% PMIDA and 6.5% NaCl, which accounted for 9.2% of the chloride in the initial solution.

2. In an apparatus similar to but larger than that described in Example 1, 466 g of a PMIDA process brine having a composition of 0.15% IDA, 0.8% MIDA, 3.0% PMIDA, 15.9% HCl and an undetermined amount of $H_3PO_3$ and $H_3PO_4$ was neutralized to pH=6.8 with 217 g of 50% NaOH. A 450 g portion of the neutralized brine was stripped at 210 mm Hg and a final pot temperature of 96° C. until 273 g of water had been removed and NaCl had precipitated. The slurry (177 g) was filtered under vacuum through a coarse sintered glass filter and the filter cake was washed with 56 g of 25.7% NaCl brine to yield 81 g of off-white salt cake after drying. The dry cake assayed as 98.5% NaCl and still contained 1.1% PMIDA. The viscous filtrate contained 9.1% PMIDA and 3.0% NaCl, which accounted for 1.9% of the chloride in the initial solution.

What is claimed is:

1. A process for the removal and recovery of NaCl from a N-phosphonomethyliminodiacetic acid (PMIDA) process waste stream which comprises neutralizing the waste stream with NaOH to a pH of about 7, evaporating off water from the neutralized waste stream at or below atmospheric pressure at a temperature of about 40 to about 130° C. until NaCl precipitates, filtering the precipitate at a temperature of about 35 to about 110° C. to separate the NaCl from the filtrate, and washing the NaCl with brine.

2. The process of claim 1 in which the water is evaporated at a temperature of about 60 to about 100° C.

3. The process of claim 1 in which the NaCl is filtered at a temperature of about 60 to about 90° C.

4. The process of claim 1 in which the NaCl is washed with brine at a temperature of about 35 to about 60° C.

5. The process of claim 1 in which the concentration of NaCl in the wash brine is about the same as that in the filtrate.

6. The process of claim 1 in which the brine wash is recycled to the neutralized waste stream.

7. The process of claim 1 in which the filtrate is further treated by air oxidation or incineration.

* * * * *